United States Patent
Zak et al.

(12)

(10) Patent No.: US 6,503,943 B1
(45) Date of Patent: Jan. 7, 2003

(54) PLATINUM COMPLEX, ITS PREPARATION AND THERAPEUTIC APPLICATION

(75) Inventors: Frantisek Zak, Brno; Adolf Mistr, Tisnov; Anna Poulova, Ivancice; Milan Melka, Hradec Kralove; Jaroslav Turanek, Jemnice; Dana Zaluska, Dolni Loucky, all of (CZ)

(73) Assignee: Pliva-Lachema, A.S., Brno (CZ)

( * ) Notice: Subject to any disclaimer, the term of this patent is extended or adjusted under 35 U.S.C. 154(b) by 0 days.

(21) Appl. No.: 09/700,514

(22) PCT Filed: May 24, 1999

(86) PCT No.: PCT/CZ99/00015

§ 371 (c)(1),
(2), (4) Date: Jan. 8, 2000

(87) PCT Pub. No.: WO99/61451

PCT Pub. Date: Dec. 2, 1999

(30) Foreign Application Priority Data

May 27, 1998 (CZ) .............................................. 1628-98

(51) Int. Cl.[7] .......................... C07B 37/02; C07F 17/02; C07F 15/00; A61K 31/715; A61K 31/28

(52) U.S. Cl. ......................... 514/492; 514/59; 556/136; 556/137; 536/112

(58) Field of Search ................................ 556/136, 137; 536/112; 514/59, 492

(56) References Cited

U.S. PATENT DOCUMENTS 6,136,336 A * 10/2000 Tanaka et al. ............... 424/434

OTHER PUBLICATIONS

Kelland et al. "Synthesis and in Vitro and In Vivo Antitumor Activity of a Series of Trans Platinum Antitumor Complexes" J. Med. Chem. 1995, 38, 3016–3024.*

* cited by examiner

*Primary Examiner*—Peter O'Sullivan
(74) *Attorney, Agent, or Firm*—Notaro & Michalos P.C.

(57) ABSTRACT

Disclosed is a platinum complex of formula (I) wherein X represents a halogen atom, B represent, independently to each other, a halogen atom, a hydroxyl group or a carboxylate group containing 1 to 6 carbon atoms, and A represents a croup —$NH_2$—R wherein R is a tricyclic hydrocarbon moiety containing 10 to 14 carbon atoms which may be optionally substituted on the tricyclic ring by one or two alkyl group(s) each containing 1 to 4 carbon atoms, and, furthermore, an inclusion complex of the above platinum complex with beta- or gamma-cyclodextrin which may be optionally substituted by hydroxyalkyl groups containing 1 to 6 carbon atoms. There is also disclosed a process for the manufacture of the complex of formula (I) based on oxidation of a complex of divalent platinum of formula (II) with hydrogen peroxide and on optional substitution of hydroxyl groups in the obtained product with carboxylate groups by action of an acylating agent. The disclosed complexes may be used as such or as a part of pharmaceutical composition in a therapy of oncologic diseases.

8 Claims, No Drawings

PLATINUM COMPLEX, ITS PREPARATION AND THERAPEUTIC APPLICATION

This application is a 371 of PCT/CZ99/00015 filed May 24, 1999.

FIELD OF THE INVENTION

The invention relates to a new platinum complex which is useful in medicinal practice for a therapy of oncological diseases. The invention further discloses a process for the preparation of the said complex, use of the complex as a pharmaceutical and pharmaceutical compositions containing that platinum complex as the active substance.

BACKGROUND OF THE INVENTION

Platinum complexes effective as cytostatic agents were introduced into medicinal practice by the end of seventieths of this century. The first pharmaceutical product based on platinum complexes was cisplatin (cis-diammine-dichloroplatinum (II) ). During further development of said complexes, tens of platinum complexes were synthetised and tested; among them, carboplatin became to be a substance which attained the biggest importance in oncology. Both the cited compounds, however, have to be administered only parenterally and neither of them is suitable for oral administration. The publication J.MED.CHEM(1995),38 (16),3016–24 discloses hexacoordinate all-trans platinum complexes bearing halogen, hydroxyl or carboxyate groups and amine groups. The difference between those complexes and the invention ones is in that the invention complexes have cis,trans,cis geometry. EP-A-0 503 830 refers to the platinum (IV) complexes having trans,trans,trans geometry and bearing cyclohexylamine group. The complexes cis,cis,trans are in fact prepared under specific conditions in very restricted extent, only, for example by means of an long-termed acetylation implemented under light radiation effect. Otherwise, the complexes trans,trans,trans are obtained under habitual acetylation conditions. As far as oral administration is concerned, some complexes of tetravalent platinum as disclosed in EP 328 274 and 423707 were shown as suitable. These complexes of tetravalent platinum have cis,trans,cis geometry and contain, apart from four halogen or carboxylate ligands, two basic assymetric groups, one of them being ammin and the second being a substituted alkyl- or cycloalklamine.

At present, platinum complexes which would express higher antitumor efficiacy in comparison with known platinum complexes are still being searched.

Now, within the present invention, certain new platinum complexes which possess higher antitumor efficiacy in comparison with platinum complexes of the prior art were found. These new complexes represent the background of the present invention.

SUMMARY OF THE INVENTION

According to a first aspect of the invention, there is provided a platinum complex of formula (I)

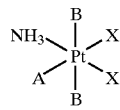
(I)

wherein
X represents a halogen atom,
B represent, independently of each other, a halogen atom, a hydroxyl group or a carboxylate group containing 1 to 6 carbon atoms, and
A represents a group —NH$_2$-R, wherein R is a tricyclic hydrocarbon moiety containing 10 to 14 carbon atoms, which may be optionally substituted on the tricyclic ring by one or two alkyl group(s) each containing 1 to 4 carbon atoms.

According to the second aspect of the invention, there is provided an inclusion complex of a platinum complex with oxidation number IV of formula I

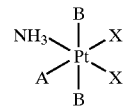
(I)

wherein
X represents a halogen atom,
B represent, idependently to each other, a halogen atom, a hydroxyl group or a carboxylate group containing 1 to 6 carbon atoms, and
A represents a group —NH$_2$—R, wherein R is a tricyclic hydrocarbon moiety containing 10 to 14 carbon atoms, which may be substituted on the tricyclic ring by one or two alkyl group(s) each containing 1 to 4 carbon atoms,
with beta- or gamma-cyclodextrin which may be optionally substituted by hydroxyalkyl groups containing 1 to 6 carbon atoms.

Especially advantageous platinum complexes of the present invention are complexes of formula (I) wherein A represents an adamantylamino group and X and B have the above defined meaning, and, furthermore, their inclusion complexes with beta- or gamma cyclodextrin which may be optionally substituted as disclosed hereinabove.

Another advantageous platinum complexes of the present invention are complexes of formula (I) wherein A represents a 3,5-dimethyladamantylamino group and X and B have the above defined meaning, and, furthermore, their inclusion complexes with beta- or gamma-cyclodextrin which may be optionally substituted as disclosed hereinabove.

In another aspect of the present invention, there is provided a process for the preparation of the platinum complex of formula (I) which is characterised in that a complex of divalent platinum of formula (II)

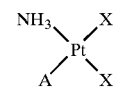
(II)

wherein X and A have the above defined meaning,
is oxidized at platinum atom by hydrogen peroxide under formation of a platinum(IV)dihydroxo-complex and, optionally,
the hydroxy groups of the said complex are substituted by carboxylate groups by action of an acylating agent.

The invention also provides a process for the preparation of an inclusion complex of the platinum complex of formula (I) with beta- or gammacyclodextrin which may be optionally substituted by a hydroxyalkyl group containing 1 to 6 carbon atoms, said process being characterized in mixing a solution of the platinum complex of formula (I) in an organic solvent with an aqueous solution of beta- or gammacyclodextrin which is optionally substituted by hydroxyalkyl groups containing 1 to 6 carbon atoms, and, in the following step, the solvents are evaporated from the obtained solution.

Still another aspect of the invention is the platinum complex of formula (I) above or its inclusion complex with beta-or gammacyclodextrin for use as a pharmaceutical.

The last aspect of the invention provides a pharmaceutical composition for therapy of oncological diseases, characterised in that it contains, as the active substance, at least one platinum complex of above formula (I) or its inclusion complex with beta-or gamma cyclodextrin which may be optionally substituted as defined above, and at least one pharmaceutical excipient.

The platinum complexes of the present invention are novel chemical compounds as until now neither these compounds have been specifically disclosed in any document of the prior art nor their properties have been characterised herein nor a method of their production has been disclosed. The utility of these compounds as active substances in the therapy of oncological diseases is likewise new and inventive as it was not possible to deduce from the known prior art by an obvious way that the presence of primary tricyclic amine ligand in tetravalent platinum complexes would lead to a basic increase of antitumor activity of the new compounds of the present invention.

Main advantages of the platinum complexes of the present invention in comparison with the so far known platinum complexes and namely in comparison with platinum complexes disclosed in the patents EP 328274 and EP 423707 are based not only on their higher efficacy at oral administration and low toxicity but namely on broader spectrum of their antitumor activity.

In further part, the invention will be described in more detail by the means of examples of concrete arrangement. It must be understood that these examples are for illustrative purposes and that they by no means limit the scope of the invention which is rather defined by the patent claims.

DETAILED DESCRIPTION OF THE INVENTION

EXAMPLE 1

Synthesis of Af-bis (Acetato)-b-(1-Adamantylamine)-c-ammin-de-dichloroplatinum (IV) Complex (Hereinafter Will be Called as "LA-12") [(OC-6-43)-Bis(Acetato)(1-Adamantylamine)Amminedichloroplatinum(IV)]

Stir 6.25 g (13.3 mmol) of b-(1-adamantylamine)-c-ammin-de-dichloro-afdihydroxoplatinum(IV) complex [(OC-6-43)-(1Adamantylamine)armminedichlorodihydroxoplatinum(IV)] at room temperature with an excess of acetic anhydride (50.2 ml, 532 mmol). During the time, a solid continuously precipitates from the original solution. After termination of the precipitation, filter the solid and wash it with a small amount of acetic anhydride and ether. After drying in a vacuum dryer, 4.28 g (58.2%) of the title product is obtained.

The identity of the obtained product was confirmed by 1H and 13C nuclear magnetic resonance spectrum and by infrared spectrum and its purity was determined by high performance liquid chromatography.

Elemental analysis of the product for $C_{14}H_{26}Cl_2N_2O_4Pt$:

|  | C (%) | H (%) | N (%) | Cl (%) |
|---|---|---|---|---|
| found | 30.24 | 4.75 | 4.99 | 12.81 |
| calculated | 30.44 | 4.74 | 5.07 | 12.84 |

EXAMPLE 2

Synthesis of af-bis(Acetato)-b-(1amino-3.5-dimethyladamantane)-c-ammin-de-dichloroplatinum (IV) Complex (hereinafter will be called as "LA-15") [(OC-6-43)-bis(acetato)(1-amino-3,5-dimethyladamantane)amminedichloroplatinum(IV)]

Stir 0.96 g (1.93 mmol) of b-(1-amino-3,5-dimethyladamantane)-c-ammin-de-dichloro-af-dihydroxoplatinum(IV) complex[(OC-6-43)-(1-amino-3,5 dimethyladam at room temperature with an excess of acetic anhydride (8 ml, 84.7 mmol). After dissolution, add 10 ml of ether to the reaction mixture. Continue in stirring until the formation of a precipitate terminates. Filter the precipitated solid ,wash with ether and dry in a vacuum dryer. The yield is 0.72 g (64.3%) of the title product.

The identity of the obtained product was confirmed by 1H and 13C nuclear magnetic resonance spectrum and by infrared spectrum and its purity was determined by high performance liquid chromatography.

Elemental analysis of the product for $C_{16}H_{30}Cl_2N_2O_4Pt$:

|  | C (%) | H (%) | N (%) | Cl (%) |
|---|---|---|---|---|
| found | 32.88 | 5.21 | 4.75 | 12.31 |
| calculated | 33.11 | 5.21 | 4.83 | 12.22 |

EXAMPLE 2a

Synthesis of b-(1-Adamantylamine)-c-ammin-de-dichloro-af-dihydroxoplatinum(IV) Complex (hereinafter will be called as LA-11)

Suspend 8.01 g (18.44 mol) of cis-(1-adamantylamine)-ammin-dichloroplatinum (II) complex in 120 ml of water at room temperature. Add a stoechiometric excess (20 ml) of 30% (w/w) aqueous solution of hydrogen peroxide to the suspension, heat the reaction mixture at 80° C. for one hour and then cool to the room temperature. Separate the solid by filtration, wash with water and dry partially. Extract and wash the product with dimethylformamide in total amount of 150 ml. Remove the rests of dimethylformamide by washing with ether. After drying in vacuum dryer, the yield is 6.45 g, i.e. 74.6% of theory (related to the starting platinum (II) complex).

Identity of the product was confirmed by infrared spectral analysis and the purity was determined by high performance liquid chromatography.

Elemental analysis of the obtained product (for $C_{10}H_{22}Cl_2N_2O_2Pt$):

|   | C (%) | H (%) | N (%) | Cl (%) |
|---|---|---|---|---|
| found | 25.75 | 4.76 | 5.94 | 15.10 |
| calculated | 25.65 | 4.74 | 5.98 | 15.14 |

EXAMPLE 3

Synthesis of inclusion complex of the compound
LA-12 with hydroxypropyl-beta-cyclodextrin
(hereinafter will be called as "inclusion drug form
of LA-l12")

Dissolve the compound LA-12 in acetone to obtain the final concentration of 20 g/l. Add hydroxypropyl-beta-cyclodextrin (164 g/l) to the obtained solution. Add slowly a buffered aqueous phase of 100 mM Hepes of pH 7.3 under stirring at room temperature to that mixture until final volume ratio of acetone and aqueous phase is 1:10. The undissolved cyclodextrin dissolves rapidly even after first additions of the aqueous phase (up to 10% of the total volume of the aqueous phase). Finally remove acetone and water from the solution of the inclusion complex by lyophilisation.

Screening of antineoplastic activity of the compounds of the present invention has been performed by testing these compounds at experiments in vivo, on animals with experimental tumors such as mice leucaemia L1210 in ascitic form (IP-L1210) or in solid form (SC-L1210) grown on DBA2 mice, Gardner lymphosarcoma in solid and ascitic form (LsG) grown on C3H mice, Ehrlich tumor in solid (STE) and ascitic form (ATE) grown on NMRI mice, tumor MC2111 (transplantable mammal adenocarcinomma) grown on DBA1 mice, metastasing melanocarcinoma B16 in solid and ascitic form (SC-B16, IP-B16) grown on C57B16 mice and Lewis metastasing lung carcinoma (LL) grown on C57B16 mice, namely by a method of V.Jelinek (Neoplasma 12,469 (1965), ibid. 7,146 (1960)).

The survival time was evaluated and the optimum dosage was calculated, apart from point estimations evaluated by Student's t-test, by proportional risk model of Cox and by the procedure of Carter (Carter W.H. et al.: Cancer Res. 42,2963 (1982)). Curves of activity drawn according to this calculation procedure allow to calculate the optimum dosage and to estimate toxic dosages. This procedure allows to evaluate not only the effect at a monotherapy but also the overall toxicity and influences of components of a combined therapy. Therefore, dependences between dose and activity were modelled and evaluated in some examples also by this method.

For purposes of this invention, the term "therapy" means an inhibition of characteristics signs and symptoms of a disease on biological objects carrying a tumor, namely an inhibition of a tumor growth and inhibition of survival time decrease of a biological object. The growth of a tumor may be observed both clinically and at experiments in vivo, i.e. on experimental animals. The evaluation of the growth of a tumor may be performed by weighing of the tumor tissue or measuring of the tumor size.

Such favourable therapeutical effect of compounds of the present invention at mice females of C3H strain was proven by decrease of the tumor weight at animals with solid form of Gardner lymphosarcoma (SC-LsG), with STE, SC-B16, SC-LL and MC2111, namely at oral administration of compounds of this group of chemicals. Statistically significant ($p \leq 0.05$) or even highly significant ($p \leq 0.01$) decrease of average mass of tumors was demonstrated in comparison with the control, i.e. untreated group.

Likewise, the compounds of the present invention prolong the survival time of suitable biological objects, e.g. of mice with IP-L1210, MC211, SC-L1210, IP-LsG and ATE tumors, marginally also of those with EP-B16 and IP-LsG, namely at oral administration. As the nature of the above used test systems is lethal, the antitumor effect of the compounds of the invention may be documented by comparison of survival time of treated animals (which survive longer) with untreated control animals. In typical experiments (see Examples), one experimental group usually consisted from ten animals and the treated groups have survived statistically significantly longer than the control, i.e. untreated groups.

For to use their antitumor effects, the disclosed compounds may be administered to suitable biological objects, namely mammals, in suitable application form and by conventional ways of administration. They may be administered alone or, advantageously, as the active substances together with whatever suitable and nontoxic pharmaceutical carrier, dissolved or suspended, e.g. in water, a buffer, a physiological saline, in a solution of methylcellulose, polyethyleneglycol, polypropyleneglycol etc. Oral administration is the most advantageous one. The optimum dose is dependent on the type of the tumor which should be treated, on the type of the biological object to be treated, on its weigth and/or body surface, on the localisation of the tumor, on its morphological type, on the dosage regimen etc. It is apparent from the performed biological tests that, e.g., the effective single dose of orally administered LA-12 is only 10 mg/kg (30 mg/m$^2$) for IP-L 1210, whereby LA-2 (see below) exhibits no effect at this dose. At intermitent administration (1st, 4th and 9th day) of a typical dose of LA-12, the optimum dose for DBA2 mice with leucaemia L1210 is 22.9 mg/kg p.o.×3 (68.7 mg/m$^2$×3) and at continual administration (1st–9th day) the optimum dose for the same mice is 9.6 mg/kg p.o.×9 (28.8 mg/m$^2$×9).

The toxicity of compounds of the invention is low; the LD50 value at NMRI mice can be found above 600 mg/kg p.o.

It is apparent that useful therapeutic effects can be expected at dosages which are absolutely nontoxic for organisms of mammals. According to the biological tests performed, the tolerable and effective single oral dose for a human can be expected on a level of 30 mg/r$^2$.

In the following tests which will demonstrate the antitumor effect of compounds of the present invention the following prior art compounds were used for reference: af-bis (acetato)-b-ammin-cd-dichloro-e-(cyclohexylamine) platinum (IV) complex [(OC-6-43)-bis(acetato) amminedichloro(cyclohexylamine)platinum(TV)] (JM216, Johnson-Matthey Technology Centre, Reafing, Berkshire, Great Britain, Kelland et al., 1993) which is hereinbelow called as compound LA-2, and cis-diammin-dichloroplatinum(II) complex which is the active substance of a medicinal preparation Platidiam 10.

EXAMPLE 4

Illustration of antitumor activity of af-bis (acetato)-
b-(1-adamantylamine)-c-ammin-de-dichloroplatinum
(IV)complex (compound (I). A=1-adamantylamine.
"LA-12") in mice after single oral administration
and comparison with af-bis (acetato)-b-ammin-cd-
dichloro-e-(cyclohexylamine)platinum (IV)complex
(compound (1). A=cyclohexylamime, code JM216-
Johnson Matthey Technology Centre. "LA2") and
with cis-diammin-dichloroplatinum(II) complex
(NSC 119875, active substance of the preparation
PLATIDIAM 10 inj.sicc.)

One hundred and fifty mouse females of DBA2 strain of approximate weigth of 18 g were sorted into fourteen groups: one reference group (21 animals) and thirteen experimental groups (9–10 animals). All animals were inoculated intraperitoneally with a lethal dose of ascitic liquid from L1210 leucaemia. Ten of the experimental groups were treated with compounds LA-12 and LA-2 in water suspensions prepared ad hoc immediately before the application. The suspensions contained such amounts of the respective compound so that the experimental animals obtained one day after the inoculation of the tumor the dosages of 160,80,40,20 and 10 mg/kg resp., in volumes of 0.2–0.4 ml. PLATIDIAM4 was applied to three groups subcutaneously, in a form of an isotonic aqueous solution prepared by dissolution of the lyophilised powder in water for injections immediately before the application. The animals were monitored to determine their survival time. The dependence of the survival time value on the applied dose was evaluated in comparison with the reference group. The single estimated time points as biological responses were evaluated by a test of equivalence of two mean values (Student's t-test) under presumption of logarithmic/normal character of distribution of temporal values and under presumption of possible unknown disseminations (Roth at al., 1962). Geometric mean value was calculated from single values of the survival time. Those mean values of the test criterium the difference of which exceeded the critical value at significance level of 5% were evaluated as statistically significant.

It has been observed that animals treated with LA-12 had statistically significant (t-test, $p \leq 0.05$) higher mean value of survival time in the dosage group of 10 mg/kg p.o., namely by 55% in comparison with the untreated control group. Platidiam, at a dose of 5 mg/kg s.c., increased the mean value of survival time by 32% against the control, this difference in values however has not been statistically significant in comparison with the control group. No effect has been proven at LA-2.

The results are summarized in the following table:

TABLE 1

Antitumor effect of compounds LA-2 and LA-12 in comparison with PLATIDIAM inj. at animals with leucaemia L1210
Mice DBA2, females, 16.6–19.1 g. Transplantation of the tumor by i.p., inoculum of $10^6$ tumor cells. Beginning with the therapy 1st day after transplantation (1 × p.o., Platidiam 1x s.c. 1st day).
The table lists, with respect to the respective dosages, the mean values of survival time, confidentiality intervals of the geometric mean for $P = 1 - \beta = 0.95$ and relative values of mean survival time as a percentage of that of the control group.

| Compound | Dosage (mg/kg) | n (j) | Geom. mean (days) | Confident. interval (days) | Survival (in % of control) | Note |
|---|---|---|---|---|---|---|
| control | 0 | 21 | 12.7 | (10.0; 16.1) | 100 | |
| Platidiam | 10 | 10 | 6.1 | (5.5; 6.8) | 48 | |
| | 5 | 10 | 16.7 | (9.4; 29.6) | >132 | 2) |
| | 2.5 | 10 | 14.2 | (8.6; 23.3) | 112 | |
| LA-2 | 160 | 10 | 8.0 | (5.2; 12.2) | 63 | |
| | 80 | 10 | 10.7 | (6.6; 17.4) | 85 | |
| | 40 | 10 | 10.3 | (6.3; 16.7) | 81 | |
| | 20 | 10 | 11.9 | (6.9; 20.4) | 94 | |
| | 10 | 10 | 12.5 | (7.2; 21.7) | 99 | |
| LA-12 | 160 | 10 | 9.3 | (5.8; 14.9) | 73 | |
| | 80 | 10 | 9.5 | (5.8; 15.6) | 75 | |
| | 40 | 10 | 12.3 | (7.8; 19.4) | 97 | |
| | 20 | 10 | 13.3 | (8.2; 21.6) | 105 | |
| | 10 | 10 | 19.6 | (14.6; 26.3) | 155 | 1) | n = amount of animals in a group

TABLE 1-continued

Antitumor effect of compounds LA-2 and LA-12 in comparison with PLATIDIAM inj. at animals with leucaemia L1210
Mice DBA2, females, 16.6–19.1 g. Transplantation of the tumor by i.p., inoculum of $10^6$ tumor cells. Beginning with the therapy 1st day after transplantation (1 × p.o., Platidiam 1x s.c. 1st day).
The table lists, with respect to the respective dosages, the mean values of survival time, confidentiality intervals of the geometric mean for $P = 1 - \beta = 0.95$ and relative values of mean survival time as a percentage of that of the control group.

| Compound | Dosage (mg/kg) | n (j) | Geom. mean (days) | Confident. interval (days) | Survival (in % of control) | Note |
|---|---|---|---|---|---|---|

1) Statistically significant difference of the mean value against the control at significance level $\alpha = 0.05$
2) One animal surviving 94th day destroyed without tumor

EXAMPLE 5

Illustration of antitumor activity of af-bis(acetato)-b-(1-adamantylamine)-c-ammin-de-dichloroplatinum (IV)complex (compound (I). A=1-adamantylamine. "LA-12") in mice after intermitent oral administration and comparison with af-bis(acetato)-b-ammin-cd-dichloro-e-(cyclohexylamine)platinum (IV)complex (compound (I). A=cyclohexylamine, code JM216 "LA-2"-Kelland et al. 1993) and with cis-diammin-dichloroplatinum(II) complex NSC 119875, active substance of the preparation PLATIDIAM 10 inj.sicc.)

In a similar experiment on animals with leucaemia L1210, the compound (I) (A=adamantylamine, LA-12) was administered repeatedly in three daily doses, namely at 1st, 4th and 9th day after innoculation together with LA-2 p.o. and Platidiam s.c. in the same regimen.

It has been observed that animals treated with LA-]2 had statistically significant (t-test, $p \leq 0.05$) higher average value of survival time in the dosage group of 4 mg/kg/day p.o.×3 (148%) in comparison with the untreated control group. The compound LA-2 exhibited the same effect (148%) only at twofold dose, i.e. in a dose of 8 mg/kg/day p.o.×3. Optimum dose of LA-12 as calculated according to Carter was only 4.55 mg/kg/day p.o.×3, while that of LA-2 was 10.96 mg/kg/day p.o.×3, i.e. more than twofold. A characteristic compound of the present invention is thus more than twice as effective as a typical compound of the above cited patents in its optimum therapeutical regimen.

The results are summarized in the following table:

TABLE 2

Antitumor effect of compounds LA-2 and LA-12 in comparison with PLATIDIAM inj. at animals with leucaemia L1210
Mice DBA2, females, 19.8–21.2 g. Transplantation of the tumor by i.p., inoculum of $10^6$ tumor cells. Beginning with the therapy 1st day after transplantation (3 × p.o., Platidiam 3x s.c. 1st ,5th and 9th day).
The table lists, with respect to the respective dosages, the mean values of survival time, confidentiality intervals of the geometric mean for $P = 1 - \alpha = 0.95$ and relative values of mean survival time as a percentage of that of the control group.

| Compound | Dosage (mg/kg/ day) | n (j) | Geom. mean (days) | Confident. interval (days) | Survival (in % of control) | Note |
|---|---|---|---|---|---|---|
| control | 0 | 10 | 15.7 | (11.6; 21.1) | 100 | |
| Platidiam | 4 | 10 | 16.6 | (14.8; 18.6) | 106 | |

TABLE 2-continued

Antitumor effect of compounds LA-2 and LA-12 in comparison with
PLATIDIAM inj. at animals with leucaemia L1210
Mice DBA2, females, 19.8–21.2 g. Transplantation of the tumor by
i.p., inoculum of $10^6$ tumor cells. Beginning with the therapy 1st day
after transplantation (3 × p.o., Platidiam 3x s.c. 1st, 5th and 9th day).
The table lists, with respect to the respective dosages, the mean values
of survival time, confidentiality intervals of the geometric mean for
$P = 1 - \alpha = 0.95$ and relative values of mean survival
time as a percentage of that of the control group.

| Compound | Dosage (mg/kg/day) | n (j) | Geom. mean (days) | Confident. interval (days) | Survival (in % of control) | Note |
|---|---|---|---|---|---|---|
|  | 2 | 10 | 26.3 | (24.5; 28.2) | 168 | 2) |
|  | 1 | 10 | 28.0 | (22.0; 35.6) | 178 | 2) |
| LA-2 | 8 | 10 | 23.2 | (16.8; 32.0) | <148 | 1),4) |
|  | 4 | 10 | 18.5 | (14.7; 23.2) | 118 |  |
|  | 2 | 10 | 20.2 | (12.4; 32.8) | >129 | 4) |
| LA-12 | 8 | 10 | 18.5 | (13.5; 25.3) | 118 |  |
|  | 4 | 10 | 23.0 | (19.8; 26.5) | 147 | 1) |
|  | 2 | 10 | 19.0 | (12.7; 28.4) | >121 | 4) | n = amount of animals in a group
Statistically significant difference of the mean value against the control at
significance level $\alpha$ = 1) 0.05, 2) 0.01, 3) 0.001 4) One animal surviving 50th day

EXAMPLE 6

Illustration of antitumor activity of af-bis (acetato-b-(1-adamantylamine)-c-ammin-de-dichloroplatinum(IV)complex (compound (1), A=1-adamantylamine, "LA-12")in mice with leucaemia L1210 after continual and intermittent oral administration and comparison with af-bis(acetato)-b-ammin-cd-dichloro-e-(cyclohexylamine)platinum (IV)complex (compound (I), A=cyclohexylamine, code JM216, "LA-2"-Kelland et al., 1993) and with cis-diammin-dichloroplatinum(II)complex (NSC 119875, active substance of the preparation PLATIDIAM 10 inj.sicc.)

In an experiment on animals with leucaemia L1210 which was arranged analogically as in Examples 4 and 5, the compound (I) (A=adamantylamine, LA-12) was administered repeatedly both in nine daily doses, namely at 1st–9th day after innoculation, and also intermittently at 1st, 4th and 9th day together with LA-2 p.o. in such a way that cumulative doses were identical in both regimens. Platidiam was administered subcutaneously.

The compound LA-12 increased statistically significantly the survival time value in comparison with the control group in the dosage of 6 mg/kg/ p.o.×9, namely by 130% and it has been evaluated as antitumor effective similarly as Platidiam in dosages 8 and 4 mg/kg s.c.×1. The compound LA-2 didnot increase statistically significantly the survival time in comparison with the control group in any of the dosage groups and is thus evaluated as antitumor uneffective.

In the intermittent regimen (1st, 5th and 9th day after inoculation) no effect was proven by means of point estimations.

The evaluation of the dose/effect dependence of LA-12 shows that continual therapeutical regimen is more advantageous at the same cummulative dose.

The results are summarized in the following table:

TABLE 3

Antitumor effect of compounds LA-2 and LA-12 in comparison with
PLATIDIAM inj. at animals with leucaemia L1210: comparison of
continual therapeutic regimen with intermittent regimen.
Mice DBA2, females, 19.3–21.4 g. Inoculation of the tumor by
i.p., inoculum of $10^6$ tumor cells. Beginning with the
therapy 1st day after inoculation (9 × p.o. 1th–9th and
3x 1th, 5th and 9th day resp., Platidiam 1x s.c. 1st day).
The table lists, with respect to the respective dosages, the mean
values of survival time, confidentiality intervals of the geometric
mean for $P = 1 - \alpha = 0.95$ and relative values
of mean survival time as a percentage of that of the control group.

| Compound | Dosage (mg/kg/day) | n (j) | Geom. mean (days) | Confident. interval (days) | Survival (in % of control) | Note |
|---|---|---|---|---|---|---|
| control | 0 | 12 | 11.6 | (7.7; 17.4) | 100 |  |
| Platidiam | 8 | 10 | 23.7 | (20.1; 27.9) | 204 | 2) |
|  | 4 | 10 | 20.2 | (15.0; 27.2) | 174 | 1) |
|  | 2 | 10 | 17.9 | (12.1; 26.5) | 155 |  |
| LA-2 | 12 | 10 | 11.5 | 7.7; 17.1) | 99 | 1–9th day |
|  | 6 | 10 | 20.0 | (11.2; 35.9) | 173 |  |
|  | 3 | 10 | 18.7 | (10.1; 34.7) | 162 |  |
| LA-12 | 12 | 10 | 13.6 | (9.0; 20.8) | 118 | 1–9th day |
|  | 6 | 10 | 16.6 | (12.7; 55.8) | 230 | 1) |
|  | 3 | 10 | 11.1 | (6.5; 19.0) | 96 |  |
| LA-2 | 36 | 10 | 15.1 | (7.5; 30.1) | 130 | 1,5,9th day |
|  | 9 | 10 | 18.6 | (10.8; 32.0) | 160 |  |
|  | 9 | 10 | 11.4 | (6.7; 19.5) | 99 |  |
| LA-12 | 36 | 10 | 15.9 | (7.6; 32.9) | 137 | 1,5,9th day |
|  | 18 | 10 | 18.3 | (9.5; 35.4) | 158 |  |
|  | 9 | 10 | 13.3 | (8.1; 21.7) | 115 |  | n = amount of animals in a group
Statistically significant difference of the mean value against the control at
significance level $\alpha$ = 1) 0.05, 2) 0.01, 3) 0.001

EXAMPLE 7

Illustration of antitumor activity of af-bis(acetato)-b-(1-adamantylamine)-c-ammin-de-dichloroplatinum (IV)complex(compound (I), A=I -adamantylamine, "LA- 12"), inclusion drug form of LA-12 and af-bis(acetato)b-(1-amino-3.5-dimethyladamantan)-c-ammin-de-dichloroplatinum (IV)complex (compound (I), A=1-amino-3.5-dimethyladamantane, "LA-15") in mice with leucaemia L1210 after continual oral administration and comparison with af-bis(acetato)-b-ammin-cd-dichloro-e-(cyclohexylamine)platinum (IV)complex (compound (I), A=cyclohexylamine, code JM216, "LA-2"-Kelland et al., 1993) and with cis-diammin-dichloroplatinum(II) complex (NSC 119875, active substance of the preparation PLATIDIAM 10 inj.sicc.)

In an experiment with animals with leucaemia L1210 which was arranged analogically as in Examples 4,5 and 6, the compound LA-12, its new drug form and compound LA-15 were administered repeatedly in nine daily doses, namely at 1st–9th day after innoculation, together with LA-2 p.o. in the same regimen. Platidiam was administered subcutaneously.

The compound LA-12, its inclusion drug form and LA-15 increased the survival time value statistically highly significant in comparison with the control group in the dosages used, namely by 130% and they have been evaluated as antitumor effective similarly as Platidiam in dosages 4 mg/kg s.c.×1 (123%) and LA-2 in the dosage 3 mg/kg/day p.o.×9 (114%).

The results are summarized in the following table:

TABLE 4

Antitumor effect of compounds LA-2, LA-12, new drug form of LA-12 and LA-15 in comparison with PLATIDIAM inj. at animals with leucaemia L1210: continual therapeutic regimen. Mice DBA2, females, 13.0–19.7 g. Inoculation of the tumor by i.p., inoculum of $1.2.10^6$ tumor cells. Beginning with the therapy 1st day after inoculation (9 × p.o. 1th–9th day, Platidiam 1x s.c. 1st day). The table lists, with respect to the respective dosages, the mean values of survival time, confidentiality intervals of the geometric mean for $P = 1 - \alpha = 0.95$ and relative values of mean survival time as a percentage of that of the control group.

| Compound | Dosage (mg/kg/day) | n (j) | Geom. mean (days) | Confident. interval (days) | Survival (in % of control) | Note |
|---|---|---|---|---|---|---|
| control | 0 | 10 | 22.5 | (19.6; 25.9) | 100 | |
| Platidiam | 4 | 10 | 50.2 | (27.9; 90.2) | >223 | 5/10 |
| LA-2 | 12 | 10 | 24.4 | (16.8; 35.3) | 108 | |
|  | 6 | 10 | 30.8 | (18.9; 50.1) | 137 | 1) |
|  | 3 | 10 | 48.1 | (41.4; 56.0) | 214 | 3) |
| LA-12 | 12 | 10 | 47.2 | (43.6; 51.2) | 210 | 3) |
|  | 6 | 10 | 38.8 | (29.7; 50.8 | 172 | 2) |
|  | 3 | 10 | 44.6 | (37.3; 53.3) | 198 | 3) |
| LA-12, drug form | 12 | 10 | 51.1 | (48.4; 53.9) | 227 | 3) |
|  | 6 | 10 | 46.4 | (39.1; 55.1) | 206 | 3) |
|  | 3 | 10 | 40.0 | (31.7; 50.4) | 177 | 3) |
| LA-15 | 12 | 10 | 29.3 | (18.1; 47.6) | 130 | |
|  | 6 | 10 | 48.8 | (41.9; 56.9) | 217 | 3) |
|  | 3 | 10 | 40.5 | (30.0; 54.8) | 180 | 2) | n = amount of animals in a group
Statistically significant difference of the mean value against the control at significance level α = 1) 0.05, 2) 0.01, 3) 0.001 4) LTS - Long Term Survivors (amount of surviving animals in a group)

EXAMPLE 8

Illustration of antitumor activity of af-bis(acetato)-b-(1-adamantylamine)-c-ammin-de-dichloroplatinum (IV)complex (compound (I), A=1-adamantylamine, "LA-12"), in mice with Garden lymphosarcoma after single oral administration and comparison with af-bis(acetato)-b-ammin-cd-dichloro-e-(cyclohexylamine)platinum (IV)complex (compound (I), A=cyclohexylamine, code JM216, "LA-2"-Kelland et al. 1993) and with cis-diammin-dichloroplatinum(II) complex (NSC 119875, active substance of the preparation PLATIDIAM 10 inj.sicc.)

Two hundred mice females of C3H strain weighing of about 25 g were sorted into ten groups, namely one control and nine experimental ones, each containing 20 animals. Lethal dose of a tumor homogenate from Gardner lymphosarcoma was transplantated subcutaneously to all animals. Experimental groups were treated with compounds LA12 and LA-2 in water suspension prepared ad hoc immediately before the application. The suspensions contained such amounts of the respective compound so that the experimental animals obtained the fifth day after the inoculation of the tumor the dosages of 32,8 and 2 mg/kg resp., in volumes of 0.2–0.4 ml; PLATIDIAM was applied once in a dose of 8,4 and 2 mg/kg s.c. Half of the animals in each dosage group was destroyed the 14th day after inoculation in ether narcosis and tumors were surgically isolated from bodies. The mass of a tumor at each of the animals was determined by weighing. The second halves of animals were left for monitoring the survival time.

It has been observed that animals treated with LA-12 had statistically significant (t-test, $p \leq 0.05$) lower average mass of a tumor (77%) at a dose of 32 mg/kg p.o. in comparison with the control group (100%). No effect has been observed at LA-2 of the prior art.

The results are summarized in the following table:

TABLE 5

Antitumor effect of compounds LA-2 and LA-12 in comparison with PLATIDIAM inj. at animals with solid form of Gardner lymphosarcoma.
Mice C3H, females, 20.7–28.3 g. Transplantation of the tumor by s.c., 0.2 ml of tumor homogenate. Beginning with the therapy 5th day after transplantation (1 × p.o., Platidiam 1x s.c. 5th day). The table lists, with respect to the respective dosages, average values of tumor mass, confidentiality intervals of the arithmetic mean for $P = 1 - \alpha = 0.95$ and relative values of mean tumor mass as a percentage of that of the control group.

| Compound | Dosage (mg/kg/day) | n (j) | Arithm. mean (g) | Confident. interval (g) | Tumor mass (%) | Note |
|---|---|---|---|---|---|---|
| control | 0 | 10 | 6.24 | (5.13; 7.35) | 100 | |
| Platidiam | 8 | 10 | 1.64 | (0.92; 2.36) | 26 | 3) |
|  | 4 | 10 | 3.68 | (3.06; 4.30) | 59 | 3) |
|  | 2 | 10 | 5.19 | (4.31; 6.06) | 83 | |
| LA-2 | 32 | 10 | 6.44 | (5.61; 7.28) | 103 | |
|  | 8 | 10 | 6.19 | (5.52; 6.87) | 99 | |
|  | 2 | 10 | 5.61 | (4.67; 6.55) | 90 | |
| LA-12 | 32 | 10 | 4.80 | (4.26; 5.34) | 77 | 1) |
|  | 8 | 10 | 5.46 | (4.43; 6.49) | 88 | |
|  | 2 | 10 | 5.02 | (4.28; 5.75) | 80 | | n = amount of animals in a group
Statistically significant difference of the mean value against the control at significance level α = 1) 0.05, 2) 0.01, 3) 0.001

EXAMPLE 9

Illustration of antitumor activity of af-bis(acetato)-b-(1-adamantylamine)-c-ammin-de-dichloroplatinum (IV)complex (compound (I), A=1-adamantylamine, "LA-12"), in mice with mammal adenocarcinoma NC2111 after repeated continual oral administration and comparison with af-bis(acetato)-b-ammin-cd-dichloro-e-(cyclohexylamine)platinum (IV)complex (compound(I), A=cyclohexylamine, code JM1216, "LA-2"-Kelland et al., 1993) and with cis-diammin-dichloroplatinum(II) complex (NSC 119875, active substance of the preparation PLATIDIAM 10 inj.sicc.)

One hundred thirty mice females of DBA1 strain weighing of about 20 g were sorted into twelves groups, namely one control and eleven experimental ones, each containing 10 animals. Lethal dose of tumor homogenate was inoculated subcutaneously to all animals. Experimental groups were treated with compounds LA-2, LA-12 and LA-15 in water suspension prepared ad hoc immediately before the application. The suspensions contained such amounts of the respective compounds so that the experimental animals obtained the dosages of 12, 6 and 3 mglg/day p.o×9 resp., in volumes of 0.2–0.4 ml; PLATIDIAM was applied once in a dose of 8 and 4 mg/kg s.c. in volume of 0.2 and 0.4 ml, the fifth day after inoculation.

The animals from the control group and from each dosage group were weighed and sizes of tumors were measured at 14th day after inoculation . One half of animals from the control group was destroyed in ether narcosis and tumors were surgically isolated from bodies. A dependence of a mass of a tumor on its size was evaluated by regression analysis. The mass of a tumor at each of the animals was determined from this regression function. The tumor masses were evaluated in case of point estimations by a test of equivalence of two mean values (Student's t-test) under presumption of normal character of distribution of mass values and under presumption of possible unknown disseminations. Arithmetic mean value was calculated from the single values of the tumor mass. Those differences in mean values at which the value of test criterium exceeded the critical value at 5% significance level were evaluated as statistically significant.

The dependence of survival time on the applied dose has been evaluated in comparison with the untreated control. The time has been evaluated analogically as at leucaemias and ascitic tumors, namely in case of estimated time points by a test of equivalence of two mean values (Student's t-test) under presumption of logarithmic/normal character of distribution of temporal values and under presumption of possible unknown disseminations (Roth Z., Josifko M., Maly V.,Trcka V.: Statisticke metody v experimentalni medicine, SZN Prague 1962, p. 278). Geometric mean value was calculated from single values of the survival time. Those mean values of the test criterium the difference of which exceeded the critical value at the 5% significance level were evaluated as statistically significant.

It has been observed that animals treated with LA-12 had statistically significant (t-test, $p \leq 0.05$) lower average mass of a tumor (86 %) at a dose of 3 mg/kg/day p.o.×9. Furthermore, they had statistically significant (t-test, $p \leq 0.05$) higher mean value of survival time (128%) in comparison with the untreated control group (100%). Other tested substances (except of Platidiam) had no statistically significant difference in point estimations of survival time in comparison with the control group.

The compound LA-12, as well as Platidiam, was evaluated as antitumor effective. No effect was observed at LA-2 of the prior art.

The results are summarized in the following table:

TABLE 6-1

Antitumor effect of compounds LA-2, LA-12 and LA-15 in comparison with PLATIDIAM inj. at animals with solid form of mammal adenocarcinoma MC2111; continual therapeutical regimen.
Mice DBA1, females, 20.4–21.8 g. Inoculation of the tumor by s.c., 0.2 ml of tumor homogenate, dilution 1:1. Beginning with the therapy 5th day after inoculation (9 × p.o., 5th–13 day, Platidiam 1 × s.c. 5th day).
The table lists, with respect to the respective dosages, mean values of survival time, confidentiality intervals of the geometric mean for P = 1-α = 0.95 and relative values of mean survival times as a percentage of that of the control group.

| Compound | Dosage (mg/kg/ day) | n (j) | Geom. mean (days) | Confident. interval (days) | Survival (in % of control) | Note LTS |
|---|---|---|---|---|---|---|
| control | 0 | 10 | 21.6 | (19.4; 24.2) | 100 | |
| Platidiam | 8 | 10 | 35.1 | (25.3; 48.7) | >162 2) | 1/10 |
| | 4 | 10 | 34.3 | (23.0; 51.3) | >158 1) | 1/10 |
| LA-2 | 12 | 10 | 21.7 | (17.9; 26.3) | 100 | |
| | 6 | 10 | 24.9 | (19.8; 32.9) | 115 | |
| | 3 | 10 | 24.5 | (21.0; 28.5) | 113 | |
| LA-12 | 12 | 10 | 25.1 | (21.9; 28.8) | 116 | |
| | 6 | 10 | 25.3 | (20.0; 32.0) | 117 | |
| | 3 | 10 | 27.7 | (24.8; 30.9) | 128 | 2) |
| LA-15 | 12 | 9 | 25.5 | (20.7; 31.4) | 118 | |
| | 6 | 10 | 27.6 | (21.8; 35.0) | 127 | |
| | 3 | 10 | 25.4 | (21.7; 29.7) | 117 | | n = amount of animals in a group
Statistically significant difference of the mean value against the control at significance level α = 1) 0.05, 2) 0.01

TABLE 6-1-continued

Antitumor effect of compounds LA-2, LA-12 and LA-15 in comparison with PLATIDIAM inj. at animals with solid form of mammal adenocarcinoma MC2111; continual therapeutical regimen.
Mice DBA1, females, 20.4–21.8 g. Inoculation of the tumor by s.c., 0.2 ml of tumor homogenate, dilution 1:1. Beginning with the therapy 5th day after inoculation (9 × p.o., 5th–13 day, Platidiam 1 × s.c. 5th day).
The table lists, with respect to the respective dosages, mean values of survival time, confidentiality intervals of the geometric mean for P = 1-α = 0.95 and relative values of mean survival times as a percentage of that of the control group.

| Compound | Dosage (mg/kg/ day) | n (j) | Geom. mean (days) | Confident. interval (days) | Survival (in % of control) | Note LTS |
|---|---|---|---|---|---|---|

LTS — Long Term Survivors; the amount of animals destroyed at 120th day

TABLE 6-2

Antitumor effect of compounds LA-2, LA-12 and LA-15 in comparison with PLATIDIAM inj. at animals with solid form of mammal adenocarcinoma MC2111; continual therapeutical regimen.
Mice DBA1, females, 20.4–21.8 g. Inoculation of the tumor by s.c., 0.2 ml of tumor homogenate, dilution 1:1. Beginning with the therapy 5th day after inoculation (9 × p.o., 5th–13 day, Platidiam 1 × s.c. 5th day).
The table lists, with respect to the respective dosages, mean values of tumor mass, confidentiality intervals of the arithmetic mean for P = 1-α = 0.95 and relative values of mean tumor masses as a percentage of that of the control group.

| Compound | Dosage (mg/kg/ day) | n (j) | Arithm. mean (g) | Confident. interval (g) | Tumor mass (%) | Note |
|---|---|---|---|---|---|---|
| control | 0 | 10 | 4.65 | (4.34; 4.96) | 100 | |
| Platidiam | 8 | 9 | 3.20 | (2.90; 3.49) | 69 | 3) |
| | 4 | 9 | 3.53 | (3.01; 4.05) | 76 | 2) |
| LA-2 | 12 | 8 | 3.59 | (2.94; 4.24) | 77 | 2) |
| | 6 | 10 | 3.86 | (3.11; 4.61) | 83 | |
| | 3 | 10 | 4.00 | (3.68; 4.32) | 86 | 2) |
| LA-12 | 12 | 10 | 4.05 | (3.82; 4.28) | 87 | 2) |
| | 6 | 10 | 3.73 | (3.25; 4.21) | 80 | 2) |
| | 3 | 10 | 4.02 | (3.63; 4.41) | 86 | 1) |
| LA-15 | 12 | 9 | 3.74 | (3.28; 4.21) | 80 | 2) |
| | 6 | 10 | 3.95 | (3.50; 4.40) | 85 | 1) |
| | 3 | 10 | 4.19 | (3.91; 4.47) | 90 | 1) | n = amount of animals in a group
Statistically significant difference of the mean value against the control at significance level α = 1) 0.05, 2) 0.01
LTS — Long Term Survivors; the amount of animals destroyed at 120th day

EXAMPLE 10

Illustration of antitumor activity of af-bis(acetato)-b-(1-adamantylamine)-c-ammin-dedichloroplatinum (IV)complex (compound (I), A=1-adamantylamine, "LA-2"), in mice with ascitic Ehrlich tumor after repeated oral administration and comparison with af-bis(acetato)-b-ammin-cd-dichloro-e-(cyclohexylamine)platinum(IV)complex (compound (I), A=cyclohexylamine, code JM216, "LA-2"-Kelland et al., 1993) and with cis-diammin-dichloroplatinum(II) complex (NSC 119875, active substance of the preparation PLATIDIAN 10 inj. sicc.)

Two hundred mice females of ICR strain weighing of about 24 g were sorted into ten groups, namely one control and nine experimental ones, each containing 20 animals Lethal dose of ascitic liquor from ATE was inoculated intraperitoneally to all animals. Experimental groups were treated with compounds LA-12 and LA-2 in water suspension prepared ad hoc immediately before the application. The suspensions contained such amounts of the respective compounds so that the experimental animals obtained the dosages of 12, 6 and 3 mg/kg/day p.o×9 resp., in volumes of 0.2–0.4 ml; PLATIDIAM was applied once in a dose of 8, 4 and 2 mg/kg s.c. in volume of 0.2 and 0.4 ml, the first day after inoculation. Half of the animals in each dosage group was destroyed the 10th day after inoculation in ether narcosis, the ascits were sucked out after laparotomy and the mass of a tumor at each of the animals was determined from the difference of mass before and after sucking out the ascit. Remaining animals were left for monitoring the survival time.

It has been observed that animals treated had lower average mass of a tumor in comparison with the untreated control (Tab. 7–1). However, the mean survival time increase was atatistically highly significant ($p \leq 0.01$) in comparison with untreated control only at LA-12 and at Platidian, but do not at LA-2 (Tab. 7–2).

TABLE 7-1

Antitumor effect of compounds LA-2 and LA-12 in comparison with PLATIDIAM inj. at animals with ascitic form of Ehrlich tumor (ATE); continual therapeutical regimen.
Mice ICR, females, 23.7–25.4 g. Inoculation of the tumor by i.p., inoculum of 0.2 ml of ascite. Beginning with the therapy 1st day after inoculation (9 × p.o., 1st–9th day, Platidiam 1 × s.c. 1st day).
The table lists, with respect to the respective dosages, mean values of tumor mass, confidentiality intervals of the arithmetic mean for $P = 1-\alpha = 0.95$ and relative values of mean tumor masses as a percentage of that of the control group.

| Compound | Dosage (mg/kg/day) | n (j) | Arithm. mean (g) | Confident. interval (g) | Tumor mass (%) | Note |
|---|---|---|---|---|---|---|
| control | 0 | 8 | 2.65 | (1.74; 3.56) | 100 | |
| Platidiam | 8 | 10 | 2.16 | (1.10; 3.22) | 82 | |
| | 4 | 10 | 2.68 | (1.81; 3.55) | 101 | |
| | 2 | 7 | 3.06 | (2.13; 3.98) | 115 | |
| LA-2 | 12 | 9 | 2.10 | (1.37; 2.83) | 79 | |
| | 6 | 7 | 2.13 | (1.20; 3.05) | 80 | |
| | 3 | 6 | 3.17 | (2.35; 3.99) | 119 | |
| LA-12 | 12 | 8 | 2.23 | (1.43; 3.02) | 84 | |
| | 6 | 9 | 2.66 | (2.00; 3.31) | 100 | |
| | 3 | 9 | 2.76 | (1.86; 3.65) | 104 | | n = amount of animals in a group; dissection 10th day

TABLE 7-2

Antitumor effect of compounds LA-2 and LA-12 in comparison with PLATIDIAM inj. at animals with ascitic form of Ehrlich tumor (ATE); continual therapeutical regimen.
Mice ICR, females, 23.7–25.4 g. Inoculation of the tumor by i.p., inoculum of 0.2 ml of ascite. Beginning with the therapy 1st day after inoculation (9 × p.o., 1st–9th day, Platidiam 1 × s.c. 1st day).
The table lists, with respect to the respective dosages, mean values of survival time, confidentiality intervals of the geometric mean for $P = 1-\alpha = 0.95$ and relative values of mean survival times as a percentage of that of the control group.

| Compound | Dosage (mg/kg/day) | n (j) | Geom. mean (days) | Confident. interval (days) | Survival (in % of control) | Note |
|---|---|---|---|---|---|---|
| control | 0 | 10 | 11.4 | (7.4; 17.6) | 100 | |
| Platidiam | 8 | 10 | 21.0 | (16.2; 27.1) | 184 | 1) |
| | 4 | 10 | 21.8 | (19.5; 24.3) | 190 | 2) |
| | 2 | 10 | 13.8 | (8.7; 21.6) | 120 | |

TABLE 7-2-continued

Antitumor effect of compounds LA-2 and LA-12 in comparison with PLATIDIAM inj. at animals with ascitic form of Ehrlich tumor (ATE); continual therapeutical regimen.
Mice ICR, females, 23.7–25.4 g. Inoculation of the tumor by i.p., inoculum of 0.2 ml of ascite. Beginning with the therapy 1st day after inoculation (9 × p.o., 1st–9th day, Platidiam 1 × s.c. 1st day).
The table lists, with respect to the respective dosages, mean values of survival time, confidentiality intervals of the geometric mean for $P = 1-\alpha = 0.95$ and relative values of mean survival times as a percentage of that of the control group.

| Compound | Dosage (mg/kg/day) | n (j) | Geom. mean (days) | Confident. interval (days) | Survival (in % of control) | Note |
|---|---|---|---|---|---|---|
| LA-2 | 12 | 10 | 12.6 | (8.4; 18.9) | 110 | |
| | 6 | 10 | 17.9 | (12.1; 26.4) | 156 | |
| | 3 | 10 | 18.4 | (11.5; 29.6) | 161 | |
| LA-12 | 12 | 10 | 15.5 | (9.3; 25.8) | 135 | |
| | 6 | 10 | 25.1 | (22.7; 27.7) | 219 | 2) |
| | 3 | 10 | 18.0 | (12.6; 25.7) | 157 | | n = amount of animals in a group
Statistically significant difference of the mean value against the control at significance level $\alpha$ = 1) 0.05, 2) 0.01

EXAMPLE 11

Illustration of antitumor activity of af-bis(acetato)-b-(1-adamantylainine)-c-ammin-de-dichloroplatinum (IV)complex (compound (I), A=1-adamantylamine, "LA-12"), inclusion drug form of LA-12 and af-bis (acetato)b-(1-amino-3.5-dimethyladamantan)c-ammin-de-dichloroplatinum (IV) complex (compound (I), A=1-amino-3.5 dimethyladamantane. "LA-15") in mice with ATE after continual and intermittent oral administration and comparison with af-bis(acetato)-b-ammin-cd-dichloro-e-(cyclohexylamine)platinum (IV)complex (compound (I). A=cyclohexylamine, code JM216, "LA-2"-Kelland et al., 1993) and with cis-diammin-dichloroplatinum(II) complex (NSC 119875, active substance of the preparation PLATIDIAM 10 inj.sicc.)

In an experiment with animals with ATE which was arranged analogically as in Example 10, the compound LA-12, its inclusion drug form and compound LA-I 5 were administered repeatedly in nine daily doses, namely at the 1st-9th day after innoculation, together with LA-2 p.o. in the same regimen. Platidiam was administered subcutaneously.

After termination of application, one half of animals in each dosage group was destroyed at 10th day after inoculation in ether narcosis, the ascits were sucked out after laparotomy and the mass of a tumor at each of the animals was determined from the difference of mass before and after sucking out the ascit. Ascitocrit in ascitic liquor of single animals was determined on microhematocrit centrifuge in heparinized capillary tubes of 75 mm length. The value of "total ascitocrit"corresponding to a mass of cells in ascitic liquor has been determined from percentage of ascitocrit and mass of the tumor. Remaining animals were left for monitoring the survival time. In these animals, the survival time was monitored on daily basis. The dependence of the survival time value on the applied dose was evaluated in comparison with the reference group.

The single estimated time points as biological responses were evaluated by a test of equivalence of two mean values (Student's t-test). Geometric mean was calculated from single values of survival time, arithmetic means were calculated from single values of tumor mass and total ascitocrit. Difference between mean values was evaluated by a test of equivalence of two mean values (Student's t-test) under presumption of normal probability distribution of mass values as well as of total ascitocrit values and of logarithmic/normal distribution of temporal values, all under presumption of possible unknown disseminations. Those diferences in mean values, whose values of a test criterium exceeded the critical value at the 5% and 1% significance level were evaluated as statistically significant and highly statistically significant, respectively.

The optimum dosage has been calculated from values of survival time according to the proportional risk model of Cox (Carter et al., 1982). Parameters of Weinbull distribution and logarithmic transformation of introductory data were used for estimation of a basic and modified survival function from experimental data.

The inclusion drug form of LA-12 has increased the survival time in comparison with control group in statistically significant way and has been evaluated as antitumor effective similarly as Platidiam in dosages 8 and 4 mg/kg s.c.×1. The compounds LA2, LA-12 and LA-15 didnot increase the survival time statistically significant in comparison with the control group (Tab. 8.1).

It has been observed that the treated animals exhibited lower average value of tumor mass in comparison with the untreated control group (Tab. 8-2) but that difference is not statistically significant.

Mean value of the mass of cell fraction of the tumor (total ascitocrit) has been statistically significant lower only in case of the compound LA-15 in a dose of 6 mg/kg/day p.o.×9 (Tab. 8–3) which represents an evidence of antitumor effect of said compound.

The results obtained are summarized in the following tables

TABLE 8-1

Antitumor effect of compounds LA-2, LA-12, inclusion drug form of LA-12 and LA-15 in comparison with PLATIDIAM inj. at animals with ascitic form of Ehrlich tumor (ATE). Continual therapeutical regimen.
Mice ICR, females, 30.1–33.7 g. Inoculation of the tumor by i.p., inoculum of $5.10^6$ tumor cells in 0.2 ml of ascit. Beginning with the therapy 1st day after inoculation (9 × p.o., 1th–9th day, Platidiam 1 × s.c. 1st day).
The table lists, with respect to the respective dosages, mean values of survival time, confidentiality intervals of the geometric mean for P = 1-α = 0.95 and relative values of mean survival times as a percentage of that of the control group.

| Compound | Dosage (mg/kg/day) | n (j) | Geom. mean (days) | Confident. interval (days) | Survival (in % of control) | Note |
|---|---|---|---|---|---|---|
| control | 0 | 10 | 8.9 | (6.6; 12.0) | 100 | |
| Platidiam | 8 | 10 | 18.5 | (13.6; 25.1) | 208 | 3) |
| | 4 | 10 | 17.5 | (15.0; 20.5) | 197 | 3) |
| | 2 | 10 | 11.4 | (7.9; 16.3) | 128 | |
| LA-2 | 12 | 10 | 9.9 | (6.4; 15.4) | 111 | |
| | 6 | 10 | 13.2 | (8.7; 20.0) | 148 | |
| | 3 | 10 | 10.1 | (6.2; 16.3) | 114 | |
| LA-12 | 12 | 10 | 11.9 | (7.1; 20.1) | 134 | |
| | 6 | 10 | 13.6 | (8.6; 21.4) | 153 | |
| | 3 | 10 | 12.7 | (8.4; 19.4) | 143 | |
| LA-12, drug form | 12 | 10 | 14.4 | (10.3; 20.0) | 162 | 1) |
| | 6 | 10 | 16.3 | (12.3; 21.5) | 183 | 1) |
| | 3 | 10 | 12.2 | (8.1; 18.5) | 131 | |
| LA-15 | 12 | 10 | 8.6 | (5.7; 12.9) | 97 | |
| | 6 | 10 | 9.6 | (6.1; 15.0) | 108 | 3) |

TABLE 8-1-continued

Antitumor effect of compounds LA-2, LA-12, inclusion drug form of LA-12 and LA-15 in comparison with PLATIDIAM inj. at animals with ascitic form of Ehrlich tumor (ATE). Continual therapeutical regimen.
Mice ICR, females, 30.1–33.7 g. Inoculation of the tumor by i.p., inoculum of $5.10^6$ tumor cells in 0.2 ml of ascit. Beginning with the therapy 1st day after inoculation (9 × p.o., 1th–9th day, Platidiam 1 × s.c. 1st day).
The table lists, with respect to the respective dosages, mean values of survival time, confidentiality intervals of the geometric mean for P = 1-α = 0.95 and relative values of mean survival times as a percentage of that of the control group.

| Compound | Dosage (mg/kg/day) | n (j) | Geom. mean (days) | Confident. interval (days) | Survival (in % of control) | Note |
|---|---|---|---|---|---|---|
| | 3 | 10 | 8.8 | (5.8; 13.4) | 99 | | n = amount of animals in a group
Statistically significant difference of the mean value against the control at significance level α = 1) 0.05, 2) 0.01, 3) 0.001

TABLE 8-2

Antitumor effect of compounds LA-2, LA-12, inclusion drug form of LA-12 and LA-15 in comparison with PLATIDIAM inj. at animals with ascitic form of Ehrlich tumor (ATE). Continual therapeutical regimen.
Mice ICR, females, 30.1–33.7 g. Inoculation of the tumor by i.p., inoculum of $5.10^6$ tumor cells in 0.2 ml of ascit. Beginning with the therapy 1st day after inoculation (9 × p.o., 1th–9th day, Platidiam 1 × s.c. 1st day).
The table lists, with respect to the respective dosages, mean values of tumor mass, confidentiality intervals of the arithmetic mean for P = 1-α = 0.95 and relative values of mean tumor mass as a percentage of that of the control group.

| Compound | Dosage (mg/kg/day) | n (j) | Arithm. mean (g) | Confident. interval (g) | Tumor mass (%) | Note |
|---|---|---|---|---|---|---|
| control | 0 | 6 | 3.93 | (1.54; 6.32) | 100 | |
| Platidiam | 8 | 8 | 2.36 | (1.08; 3.64) | 60 | |
| | 4 | 6 | 3.53 | (1.93; 3.13) | 90 | |
| | 2 | 7 | 2.83 | (1.14; 4.52) | 72 | |
| LA-2 | 12 | 8 | 2.74 | (1.73; 3.75) | 70 | |
| | 6 | 5 | 2.32 | (0.84; 3.80) | 59 | |
| | 3 | 7 | 3.53 | (2.15; 4.91) | 90 | |
| LA-12 | 12 | 5 | 1.86 | (0.27; 3.45) | 47 | |
| | 6 | 6 | 3.07 | (1.92; 4.21) | 78 | |
| | 3 | 5 | 4.32 | (3.24; 5.40) | 110 | |
| LA-12, drug form | 12 | 7 | 4.03 | (1.30; 6.76) | 102 | |
| | 6 | 7 | 4.13 | (2.21; 6.05) | 105 | |
| | 3 | 7 | 3.93 | (2.24; 5.62) | 100 | |
| LA-15 | 12 | 3 | 3.77 | (1.53; 6.01) | 96 | |
| | 6 | 6 | 2.08 | (1.00; 3.16) | 53 | |
| | 3 | 7 | 3.51 | (2.12; 4.91) | 89 | | n = amount of animals in a group, dissection 10th day

TABLE 8-3

Antitumor effect of compounds LA-2, LA-12, inclusion drug form of LA-12 and LA-15 in comparison with PLATIDIAM inj. at animals with ascitic form of Ehrlich tumor (ATE). Continual therapeutical regimen.
Mice ICR, females, 30.1–33.7 g. Inoculation of the tumor by i.p., inoculum of $5.10^6$ tumor cells in 0.2 ml of ascit. Beginning with the therapy 1st day after inoculation (9 × p.o., 1th–9th day, Platidiam 1 × s.c. 1st day).
The table lists, with respect to the respective dosages, mean values of tumor mass, confidentiality intervals of the arithmetic mean for $P = 1-\alpha = 0.95$ and relative values of mean tumor mass as a percentage of that of the control group.

| Compound | Dosage (mg/kg/day) | n (j) | Arithm. mean (g) | Confident. interval (g) | Total ascito-crit 3) (%) | Note |
|---|---|---|---|---|---|---|
| control | 0 | 6 | 0.68 | (0.59; 0.78) | 100 | |
| Platidiam | 8 | 5 | 0.68 | (0.62; 0.75) | 100 | |
| | 4 | 6 | 0.80 | (0.54; 1.00) | 116 | |
| | 2 | 7 | 0.79 | (0.39; 1.18) | 115 | |
| LA-2 | 12 | 8 | 0.65 | (0.49; 0.82) | 95 | |
| | 6 | 5 | 0.69 | (0.34; 1.03) | 100 | |
| | 3 | 6 | 0.74 | (0.64; 0.83) | 108 | |
| LA-12 | 12 | 5 | 0.44 | (0.19; 0.69) | 64 | |
| | 6 | 6 | 0.68 | (0.46; 0.89) | 99 | |
| | 3 | 5 | 0.68 | (0.31; 1.06) | 100 | |
| LA-12, drug form | 12 | 7 | 0.80 | (0.46; 1.15) | 117 | |
| | 6 | 7 | 0.60 | (0.40; 0.81) | 88 | |
| | 3 | 7 | 0.93 | (0.24; 0.62) | 99 | |
| LA-15 | 12 | 3 | 0.82 | (0.14; 1.78) | 120 | |
| | 6 | 6 | 0.40 | (0.19; 0.61) | 59 | 2) |
| | 3 | 7 | 0.84 | (0.71; 0.97) | 123 | 1) | n = amount of animals in a group, dissection 10th day
Statistically significant difference of the mean value against the control at significance level $\alpha$ = 1) 0.05, 2) 0.01
3) Total ascitocrit - mass of cell fraction of a tumor

What is claimed is:

1. A platinum complex with oxidation number IV of formula (I)

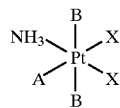

wherein

X represents a halogen atom,

B represent, independently to each other, a halogen atom, a hydroxyl group or a carboxylate group containing 1 to 6 carbon atoms, and A represents a group —NH$_2$—R, wherein R is a tricyclic hydrocarbon moiety containing 10 to 14 carbon atoms, which may be optionally substituted on the tricyclic ring by one or two alkyl group(s) each containing 1 to 4 carbon atoms.

2. An inclusion complex of a platinum complex with oxidation number IV of formula (I)

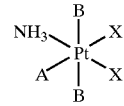

wherein

X represents a halogen atom,

B represent, independently to each other, a halogen atom, a hydroxyl group or a carboxylate group containing 1 to 6 carbon atoms, and A represents a group —NH$_2$—R, wherein R is a tricyclic hydrocarbon moiety containing 10 to 14 carbon atoms, which may be optionaly substituted on the tricyclic ring by one or two group(s) each contaning 1 to 4 carbon atoms, with beta- or gamma-cyclodextrin which may be optionally substituted by hydroxyalkyl groups containing 1 to 6 carbon atoms.

3. A complex according to claim 1 of formula (I) wherein A represents an adamantylamino group and X and B have the meaning as defined in claim 1.

4. A complex according to claim 1 of formula (I) wherein A represents a 3,5 dimethyladamantylamino group and X and B have the meaning as defined in claim 1.

5. A process for the preparation of the platinum complex of formula (I) according to claim 1 characterized in that a complex of divalent platinum of formula (II)

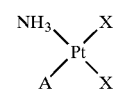

wherein X and A have the meaning as defined in claim 1 is oxidized at platinum atom by hydrogen peroxide under formation of a platinum(IV)dihydroxo-complex and, optionally, the hydroxy groups of the said complex are substituted with carboxylate groups by action of an acylating agent.

6. A process for the preparation of an inclusion complex of the platinum complex of formula (I) with beta- or gammacyclodextrin which may be optionally substituted by hydroxyalkyl groups containing 1 to 6 carbon atoms according to claim 2, said process being characterized in mixing a solution of the platinum complex of formula (I) in an organic solvent with an aqueous solution of beta- or gamma cyclodextrin which is optionally substituted by hydroxyalkyl groups containing 1 to 6 carbon atoms, following by evaporation of the solvents from the obtained solution.

7. The platinum complex of formula (I) or its inclusion complex with beta-or gammnacyclodextrin according to claim 1 for use as a pharmaceutical.

8. A pharmaceutical composition for therapy of oncological diseases characterised in that it contains at least one platinum complex of formula (I) or its inclusion complex with beta- or gamma cyclodextrin according to claim 1 as the active substance, and at least one pharmaceutical excipient.

* * * * *